(12) United States Patent
Kokish

(10) Patent No.: US 6,840,081 B2
(45) Date of Patent: Jan. 11, 2005

(54) ASSEMBLY FOR CRIMPING AN INTRALUMINAL DEVICE OR MEASURING THE RADIAL STRENGTH OF THE INTRALUMINAL DEVICE AND METHOD OF USE

(75) Inventor: Arkady Kokish, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/298,424

(22) Filed: Nov. 18, 2002

(65) Prior Publication Data

US 2003/0070469 A1 Apr. 17, 2003

Related U.S. Application Data

(63) Continuation-in-part of application No. 09/997,783, filed on Nov. 28, 2001, now Pat. No. 6,651,478, which is a continuation-in-part of application No. 09/636,093, filed on Aug. 10, 2000, now Pat. No. 6,568,235.

(51) Int. Cl.[7] .............................................. B21D 41/04
(52) U.S. Cl. ....................................... 72/402; 29/283.5
(58) Field of Search .......................... 72/402; 29/283.5, 29/282, 237, 751

(56) References Cited

U.S. PATENT DOCUMENTS

| | | |
|---|---|---|
| 141,992 A | 8/1873 | Carr |
| 430,928 A | 6/1890 | Doty |
| 579,214 A | 3/1897 | Adams |

(List continued on next page.)

FOREIGN PATENT DOCUMENTS

| | | | |
|---|---|---|---|
| CA | 2211694 | 2/1998 | |
| DE | 464004 | 7/1928 | |
| DE | 515662 | * 1/1931 | ................. 72/402 |

(List continued on next page.)

OTHER PUBLICATIONS

U.S. Appl. No. 09/928,877 filed Sep. 12, 1997.
U.S. Appl. No. 09/032,472 filed Feb. 26, 1998.
U.S. Appl. No. 09/069,010 filed Apr. 28, 1998.
U.S. Appl.. No. 09/401,705 filed Sep. 23, 1999.
U.S. Appl. No. 09/475,694 filed Dec. 30, 1999.
User Manual *TOMINATOR™ Stent Crimping Equipment* (Undated).
Bard XT Stent Brochure: *The eXTraordinary Stent* (Undated).
*Corporate Profile—Machine Solutions, Inc.*, Reprinted from *European medical Device manufacturer*, Jul./Aug. 2000 • Copyright © 2000 Canon Communications LLC.
MSI Equipment pages, From www.machinesolutions.org. Copyright © 2002 Machine Solutions, Inc.

*Primary Examiner*—Daniel C. Crane
(74) *Attorney, Agent, or Firm*—Fulwider Patton Lee & Utecht, LLP

(57) ABSTRACT

An assembly is provided which can crimp or compress an intraluminal device or measure the radial strength of an intraluminal device. The device includes a first disk and a second disk for imparting movement to a number of spaced apart moving elements attached to linear sliders on the first disk. In one configuration, rotational movement is imparted to the second disk which causes the tips of the moving elements to move is a linear direction toward the center of the opening formed by the elements thereby closing in on the device. In another configuration, rotational movement is imparted to the first disk and the tips move along an arcuate path from the perimeter of the opening toward the center of the opening.

25 Claims, 13 Drawing Sheets

U.S. PATENT DOCUMENTS

| | | | |
|---|---|---|---|
| 696,289 A | 3/1902 | Williams | |
| 852,290 A | 4/1907 | Neal | |
| 915,184 A | 3/1909 | Keirn | |
| 1,045,886 A | 12/1912 | Reay | |
| 1,230,561 A | 6/1917 | Chige | |
| 1,268,171 A | 6/1918 | Spaulding | |
| 1,493,515 A * | 5/1924 | Berthold | 72/402 |
| 1,758,261 A | 5/1930 | Leland | |
| 2,079,498 A * | 5/1937 | Douglas | 72/402 |
| 2,452,857 A | 11/1948 | Mesaros | |
| 2,465,433 A | 3/1949 | Doniger | |
| 2,553,479 A | 5/1951 | Schmarje et al. | |
| 2,964,088 A | 12/1960 | Erath | |
| 3,164,042 A | 1/1965 | Hanna et al. | |
| 3,203,078 A * | 8/1965 | Ustin | 29/862 |
| 3,350,908 A | 11/1967 | Andrews et al. | |
| 3,439,519 A | 4/1969 | Gerding | |
| 3,496,684 A | 2/1970 | Banning et al. | |
| 3,568,495 A | 3/1971 | Duffield et al. | |
| 3,619,885 A | 11/1971 | Dischler | |
| 3,695,087 A * | 10/1972 | Tuberman | 72/402 |
| 3,898,897 A | 8/1975 | Jauhiainen | |
| 4,043,172 A | 8/1977 | Schmittou | |
| 4,070,745 A | 1/1978 | Schimmelman | |
| 4,107,964 A | 8/1978 | Smith | |
| 4,215,871 A | 8/1980 | Hirsch et al. | |
| 4,353,240 A | 10/1982 | Undin et al. | |
| 4,373,923 A | 2/1983 | Kilwin | |
| 4,379,397 A | 4/1983 | Langr | |
| 4,454,657 A * | 6/1984 | Yasumi | 33/644 |
| 4,455,854 A | 6/1984 | Ermolovich et al. | |
| 4,468,224 A | 8/1984 | Enzmann et al. | |
| 4,576,142 A | 3/1986 | Schiff | |
| 4,606,347 A | 8/1986 | Fogarty et al. | |
| 4,614,107 A * | 9/1986 | Norin | 72/402 |
| 4,644,936 A | 2/1987 | Schiff | |
| 4,681,092 A | 7/1987 | Zimmerman | |
| 4,697,573 A | 10/1987 | Schiff | |
| 4,703,546 A | 11/1987 | Gilbert | |
| 4,786,271 A | 11/1988 | Menn | |
| 4,838,264 A | 6/1989 | Bremer et al. | |
| 4,864,924 A | 9/1989 | Storace | |
| 4,901,707 A | 2/1990 | Schiff | |
| 4,907,336 A | 3/1990 | Gianturco | |
| 4,961,291 A | 10/1990 | Lagassee | |
| 4,987,722 A | 1/1991 | Koebbeman | |
| 5,132,066 A | 7/1992 | Charlesworth et al. | |
| 5,133,732 A | 7/1992 | Wiktor | |
| 5,183,085 A | 2/1993 | Timmermans | |
| 5,189,786 A | 3/1993 | Ishikawa et al. | |
| 5,195,539 A | 3/1993 | Dyrud et al. | |
| 5,207,960 A | 5/1993 | Moret de Rocheprise | |
| 5,209,143 A | 5/1993 | Sweet | |
| 5,209,799 A | 5/1993 | Vigil | |
| 5,216,263 A * | 6/1993 | Paoli | 257/88 |
| 5,217,434 A | 6/1993 | Arney | |
| 5,263,969 A | 11/1993 | Phillips | |
| 5,329,797 A | 7/1994 | Calhoun | |
| 5,336,234 A | 8/1994 | Vigil et al. | |
| 5,352,197 A | 10/1994 | Hammersmark et al. | |
| 5,437,083 A | 8/1995 | Williams et al. | |
| 5,456,667 A | 10/1995 | Ham et al. | |
| 5,458,615 A | 10/1995 | Klemm et al. | |
| 5,465,716 A | 11/1995 | Avitall | |
| 5,476,505 A | 12/1995 | Limon | |
| 5,481,893 A | 1/1996 | Barjasteh et al. | |
| 5,540,124 A | 7/1996 | Srhoj | |
| 5,546,646 A | 8/1996 | Williams et al. | |
| 5,626,474 A | 5/1997 | Kukla et al. | |
| 5,626,604 A | 5/1997 | Cottone, Jr. | |
| 5,628,754 A | 5/1997 | Shevlin et al. | |
| 5,630,830 A | 5/1997 | Verbeek | |
| 5,653,691 A | 8/1997 | Rupp et al. | |
| 5,658,181 A | 8/1997 | Brown, II | |
| 5,672,169 A | 9/1997 | Verbeek | |
| 5,693,066 A | 12/1997 | Rupp et al. | |
| 5,695,515 A | 12/1997 | Orejola | |
| 5,715,723 A | 2/1998 | Owens | |
| 5,725,519 A | 3/1998 | Penner et al. | |
| 5,727,411 A | 3/1998 | Sakakibara et al. | |
| 5,738,674 A | 4/1998 | Williams et al. | |
| 5,746,764 A | 5/1998 | Green et al. | |
| 5,759,474 A | 6/1998 | Rupp et al. | |
| 5,782,855 A | 7/1998 | Lau et al. | |
| 5,782,903 A | 7/1998 | Wiktor | |
| 5,783,227 A | 7/1998 | Dunham | |
| 5,785,715 A | 7/1998 | Schatz | |
| 5,787,572 A | 8/1998 | Toms et al. | |
| 5,795,289 A | 8/1998 | Wyttenbach | |
| 5,810,838 A | 9/1998 | Solar | |
| 5,810,871 A | 9/1998 | Tuckey et al. | |
| 5,810,873 A | 9/1998 | Morales | |
| 5,836,952 A | 11/1998 | Davis et al. | |
| 5,860,966 A | 1/1999 | Tower | |
| 5,893,852 A | 4/1999 | Morales | |
| 5,893,867 A | 4/1999 | Bagaoisan et al. | |
| 5,911,452 A | 6/1999 | Yan | |
| 5,920,975 A | 7/1999 | Morales | |
| 5,931,851 A | 8/1999 | Morales | |
| 5,938,696 A | 8/1999 | Goicoechea et al. | |
| 5,944,735 A | 8/1999 | Green et al. | |
| 5,947,993 A | 9/1999 | Morales | |
| 5,948,191 A | 9/1999 | Solovay | |
| 5,951,569 A | 9/1999 | Tuckey et al. | |
| 5,972,016 A | 10/1999 | Morales | |
| 5,974,652 A | 11/1999 | Kimes et al. | |
| 6,009,614 A | 1/2000 | Morales | |
| 6,024,737 A | 2/2000 | Morales | |
| 6,051,002 A | 4/2000 | Morales | |
| 6,063,102 A | 5/2000 | Morales | |
| 6,082,990 A | 7/2000 | Jackson et al. | |
| 6,092,273 A | 7/2000 | Villareal | |
| 6,108,886 A | 8/2000 | Kimes et al. | |
| 6,125,523 A | 10/2000 | Brown et al. | |
| 6,141,855 A | 11/2000 | Morales | |
| 6,167,605 B1 * | 1/2001 | Morales | 29/282 |
| 6,176,116 B1 * | 1/2001 | Wilhelm et al. | 72/409.12 |
| 6,510,722 B1 * | 1/2003 | Ching et al. | 72/402 |
| 2001/0001890 A1 | 5/2001 | Austin | |

FOREIGN PATENT DOCUMENTS

| | | | |
|---|---|---|---|
| DE | 297 14857 U1 | 11/1997 | |
| DE | 198 13 854 | 9/1999 | |
| EP | 0 303 889 B1 | 6/1993 | |
| EP | 0 303 889 B1 | 9/1993 | |
| EP | 0 562 478 B1 | 12/1994 | |
| EP | 0 630 623 A2 | 12/1994 | |
| EP | 0 630 623 A3 | 12/1994 | |
| EP | 0 697 226 A1 | 2/1996 | |
| EP | 0 826 346 A1 | 3/1998 | |
| EP | 0 873 731 A1 | 10/1998 | |
| EP | 0 938 877 A2 | 9/1999 | |
| EP | 0 938 880 A2 | 9/1999 | |
| EP | 0 938 880 A3 | 11/1999 | |
| FR | 975797 | 3/1951 | |
| GB | 159065 | 2/1921 | |
| GB | 1202431 * | 8/1970 | 72/402 |
| GB | 2 088 811 A | 6/1982 | |
| JP | 56-160829 | 12/1981 | |
| JP | 02180275 | 7/1990 | |

| | | | | | | |
|---|---|---|---|---|---|---|
| JP | 445187 | 7/1992 | | WO | WO 98/14120 | 4/1998 |
| JP | 7-47135 | 2/1995 | | WO | WO 98/19633 | 5/1998 |
| JP | 7-67967 | 3/1995 | | WO | WO 99/43473 | 9/1999 |
| JP | 11-19230 | 1/1999 | | WO | WO 99/55406 | 11/1999 |
| SU | 189293 | * 11/1966 | ................. 72/402 | WO | WO 01/21103 | 3/2001 |
| WO | WO 93/06780 | 4/1993 | | | | |
| WO | WO 97/09946 | 3/1997 | | * cited by examiner | | |

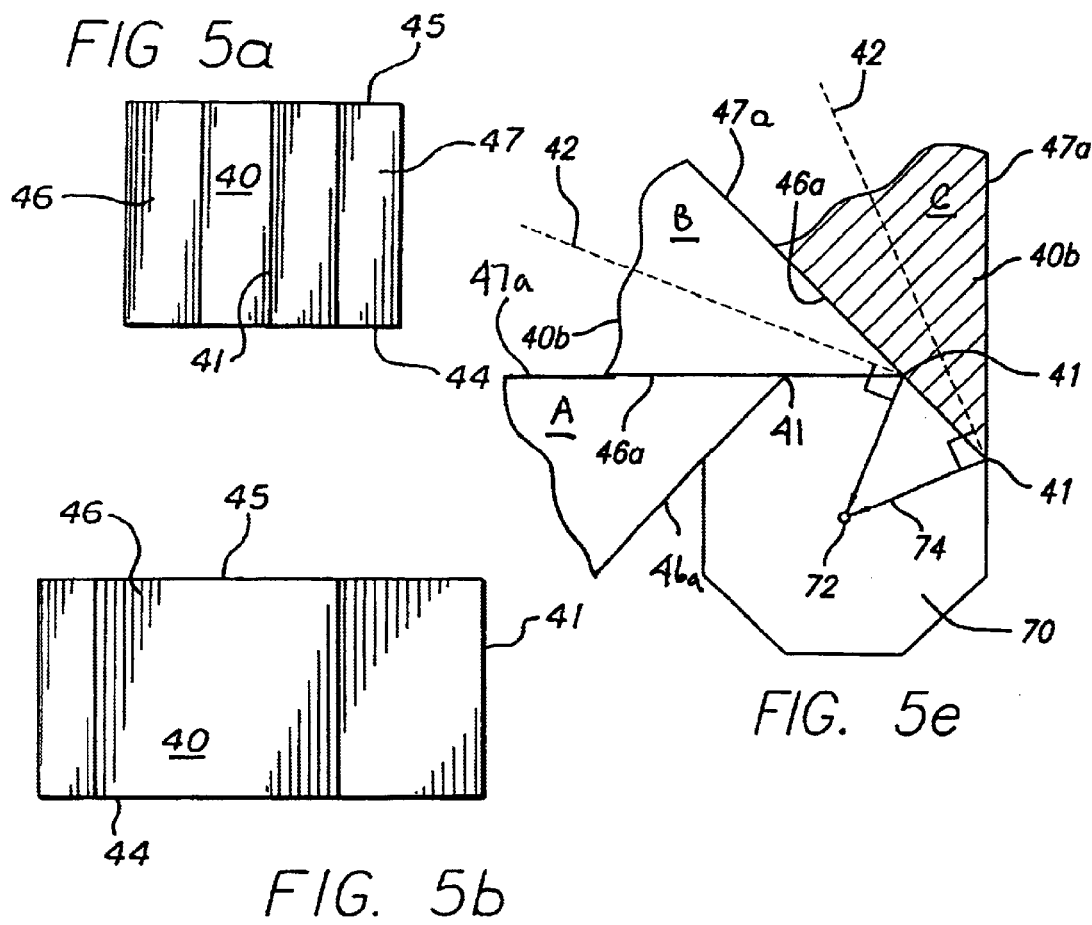
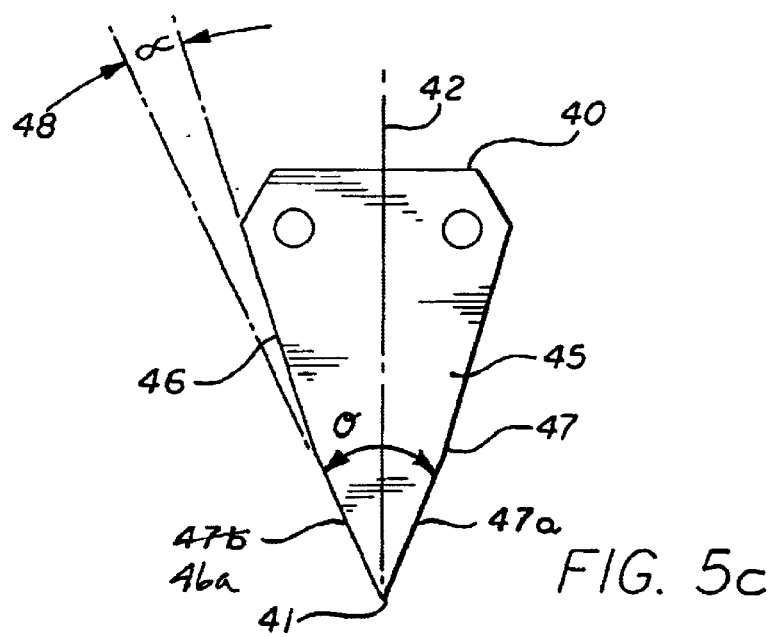

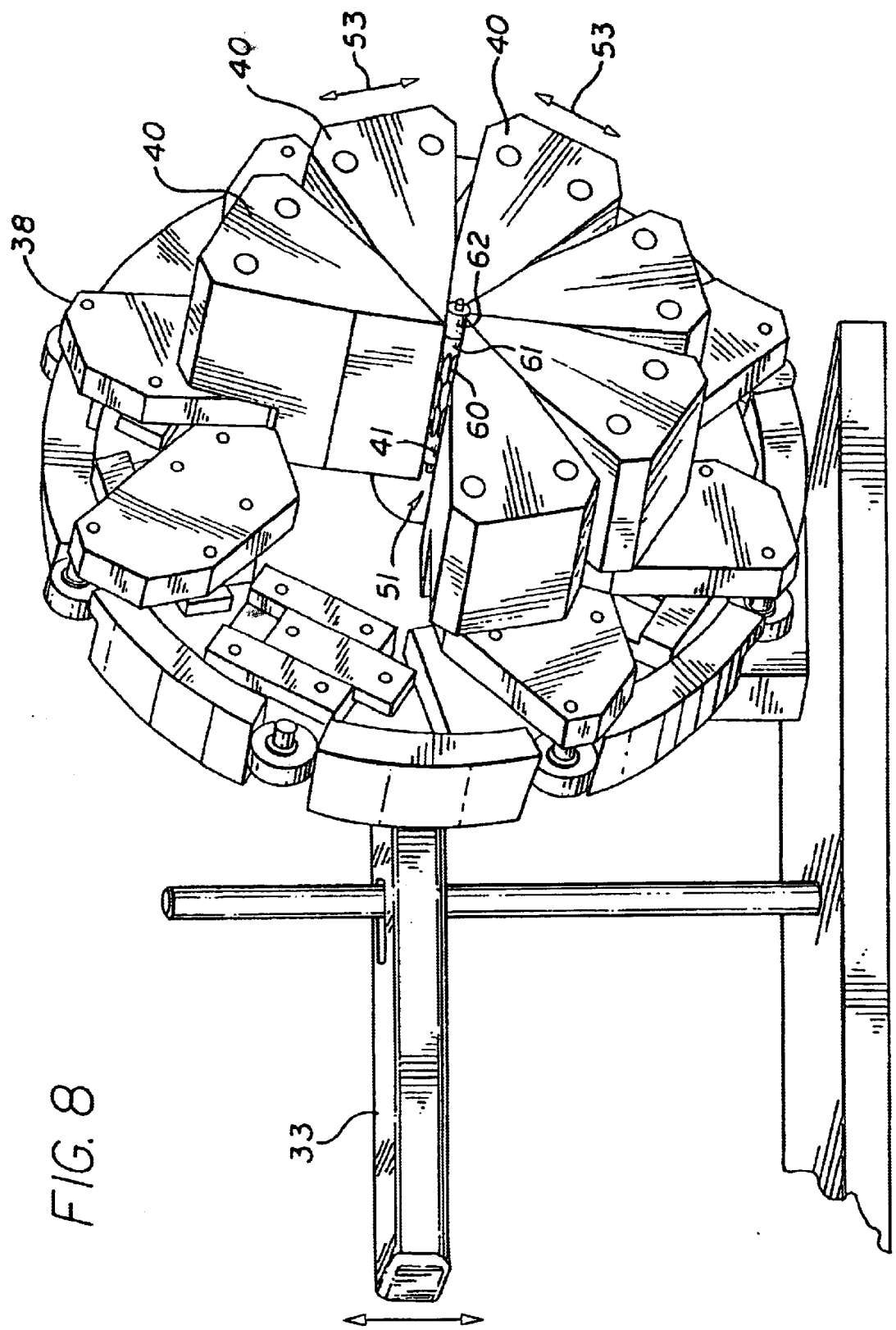

ASSEMBLY FOR CRIMPING AN INTRALUMINAL DEVICE OR MEASURING THE RADIAL STRENGTH OF THE INTRALUMINAL DEVICE AND METHOD OF USE

RELATED APPLICATIONS

This is a continuation-in-part of application Ser. No. 09/997,783, filed Nov. 28, 2001 now U.S. Pat. No. 6,651,478 which is a continuation-in-part of application Ser. No. 09/636,093, filed Aug. 10, 2000 now U.S. Pat. No. 6,568,235.

BACKGROUND OF THE INVENTION

The present invention relates to an apparatus for loading an intraluminal device, such as a stent or an embolic device such as a filter, onto the distal end of a catheter assembly similar to those used, for example, in percutaneous transluminal coronary angioplasty (PTCA) procedures or in percutaneous transluminal angioplasty (PTA) procedures. The present invention device is useful in crimping balloon-expandable stents and self-expanding stents.

In typical PTCA procedures, a guiding catheter is percutaneously introduced into the cardiovascular system of a patient through the brachial or femoral arteries and advanced through the vasculature until the distal end of the guiding catheter is in the ostium of the aorta leading to the coronary arteries. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop at or near the treatment area, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the treated area. The stent is transported in its low profile delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and typically through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, nonuniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is sometimes done by hand, which can be unsatisfactory due to the uneven application of force resulting in non-uniform crimps. In addition, it is difficult to visually judge when a uniform and reliable crimp has been applied.

Some self-expanding stents are difficult to load by hand into a delivery device such as a catheter. Self-expanding stents typically are compressed or crimped to a small diameter and then inserted into a delivery catheter where the stent remains until it is pushed out and expands into the vessel. Further, the more the stent is handled the higher the likelihood of human error, which would be antithetical to a properly crimped stent. Accordingly, there is a need in the art for a device for reliably crimping or compressing a self-expanding stent and inserting it into a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, commonly owned and assigned U.S. Pat. Nos. 5,437,083 and 5,546,646 to Williams et al.

Yet another stent crimping tool is known in the art as the BARD XT, which is actually a stent loader. It is constructed of a tubular body with a ball at one end connected to a plurality of long, thin strips passing through the rigid tubular body. An uncrimped stent is placed over the plurality of long, thin strips, which hold the stent in an expanded state. The balloon portion of a catheter is inserted into the cylindrical space formed by the plurality of strips. When the user pulls on the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps, and they are unsuitable for use by physicians in a cath lab who desire to crimp the stent onto the balloon catheter.

SUMMARY OF THE INVENTION

The present invention provides for a stent crimping or compressing assembly that is easy to use, and provides a tight and reliable crimped stent onto the distal portion of a stent delivery catheter. Preferably, the stent crimping assembly is used to crimp an expandable stent onto the balloon portion of a catheter, however, the device can be used with self-expanding stents as well. The terms crimping and compressing as used herein are meant to be interchangeable and mean that the diameter of the stent is reduced to some degree. Typically, balloon-expandable stents are known by persons having ordinary skill in the art to be "crimped" onto the balloon portion of a catheter while self-expanding stents are compressed onto a mandrel or sheath and then inserted into a catheter. Also, references to "stent crimping assembly" as used herein is not meant to be limiting since the assembly can be used as a measuring device to accurately measure the radial strength of a stent. Thus, for ease of reference, the device has been referred to throughout as a stent crimping assembly, but it also is used to measure the radial strength of a stent. Further, while reference is made herein to crimping or compressing "stents," the invention can be used with any intraluminal device to reduce the diameter or measure radial strength. Thus, the invention is particularly useful with stents, grafts, tubular prostheses, embolic devices, embolic filters, and embolic retrieval devices.

In one embodiment, the crimping assembly includes a plurality of spaced apart moving elements. These moving elements may have any one of a variety of shapes such as a triangular wedge or a knife blade. Each element has a first side and a second side joining at a tip. The first side includes a substantially linear region, a portion of which contacts the stent during the crimping process. The moving elements are arranged such that the tip of each element is spaced from the first side of an adjacent moving element and is located more adjacent to the first side of the adjacent element than the second side of the adjacent element. The first side of each moving element forms an exterior angle with the first side of each adjacent moving element. Depending on the number of moving elements the exterior angle may be acute or obtuse. For example, an assembly with eight moving elements would have acute exterior angles while and assembly with three moving elements would have obtuse exterior angles. The moving elements are arranged relative to each other to form an opening having a center. Each moving element is configured for movement. To this end, the moving elements are associated with a first disk and a second disk which are configured for rotational movement relative to each other. As one of the first and second disks rotates, the tip of each moving element moves toward the center of the opening formed by the moving elements.

In a detailed aspect, the assembly is configured such that the first disk is fixed in position while the second disk is allowed to rotate relative to the first disk. When the second disk is rotated in one direction, the tip of each moving element moves in a direction substantially perpendicular to the bisect of its associated exterior angle, toward the center of the opening. Conversely, when the second disk is rotated in the other direction, the tip of each moving element moves in a direction substantially perpendicular to the bisect of its associated exterior angle, away from the center of the opening. In another detailed aspect, the assembly is configured such that the second disk is fixed in position while the first disk is allowed to rotate relative to the second disk. When the first disk is rotated in one direction, the tip of each moving element moves along an arcuate path from a point on the perimeter of the opening, toward the center of the opening. When the first disk is rotated the other way, the tip of each moving element moves along an arcuate path away from the center of the opening.

It is an important feature of the invention that there is substantially frictionless movement among the elements. Accordingly, there is a space between adjacent moving elements along the entire length of the moving elements in order to substantially eliminate frictional contact between the elements. In some configurations, the space may be substantially uniform along the entire length of the moving elements. In other configurations, the space may vary in a tapered like fashion along the element length. In still other configurations, the space may vary in some regions and be uniform in others.

In one embodiment of the invention, the portion of the assembly including the first disk and the second disk can be rotated a preselected number of degrees N to more uniformly crimp the stent. For example, if eight moving elements are used to crimp the stent, under magnification the stent will have the appearance of an octagon. By rotating or indexing the assembly, including the first disk and second disk, and crimping a number of times at a preselected number of degrees N, a more uniformly crimped stent is obtained. For example, in one embodiment the assembly may be rotated 5°, and the stent then crimped. The assembly is then rotated five more degrees, and the stent crimped again, and so on up to 45° rotation in one direction, and 45° rotation in the opposite direction. In this manner, the stent is uniformly crimped and has the appearance, under magnification, of a substantially perfect cylinder.

In one method of crimping an intraluminal device onto the catheter, the crimping assembly previously described is provided. Rotational movement is imparted to one of the first and second disks which translates movement to the moving elements. During this movement, the tips of the moving elements move along a path away from the center of the opening formed by the moving elements, thereby increasing the size of the opening formed by the moving elements. A device that has been premounted on the distal portion of a catheter is positioned within the opening. Rotational movement is imparted to the previously rotated disk which again translates movement to the moving elements. During this movement, the tips of the moving elements move along a path toward the center of the opening and a portion of the first sides of the moving elements move into contact with the intraluminal device. The device is crimped onto the catheter by continuing to apply rotational movement to move the tips of the moving elements along a path toward the center of the opening. After the device is crimped onto the catheter, rotational movement is again imparted to the previously rotated disk which translates movement to the tips of the moving elements along a path away from the center of the opening, thereby allowing for the removal of the intraluminal device and catheter from the compressing assembly.

In one embodiment, the crimping device operates as described to crimp a self-expanding stent onto a mandrel. Typically, self-expanding stents are formed of a nickel-titanium alloy that exhibits shape memory effects, super-elastic effects, or both. The stent can be cooled by dry ice or other similar cooling means and then mounted on the mandrel where it is tightly crimped onto the mandrel where it is tightly crimped onto the mandrel while it is cooled. The stent is then slipped off of the mandrel and inserted into a catheter for subsequent use to repair a vessel. It may be necessary to place the stent crimping assembly in a chamber so that the chamber can be cooled to a temperature below that which martensite forms so that the stent is more malleable and easily crimped onto the mandrel.

In another embodiment of the invention, the device is used to measure the radial force of a stent. In this configuration, instead of crimping a stent, an expanded or unexpanded stent is placed in the device with the moving elements in the open position. The moving elements are moved toward the closed position as previously described and into contact with the stent. The radial force of the stent is measured by continuing to move the moving elements toward the closed position. The radial force of the stent is measured by using strain gauges, the geometric position of the moving elements, or similar means, to measure the radial resistance of the stent as the wedges continue to move toward the closed position.

These and other advantages of the present invention will become more apparent from the following description thereof when taken in conjunction with the following drawings.

BRIEF DESCRIPTION OF THE DRAWINGS

FIG. 5a depicts a front view of the moving element.

FIG. 5b depicts a side view of the moving element.

FIG. 5c depicts a top view of the moving element.

FIG. 5e depicts the paths traveled by the moving elements in one configuration of the assembly.

DETAILED DESCRIPTION OF THE PREFERRED EMBODIMENTS

Figure 1:
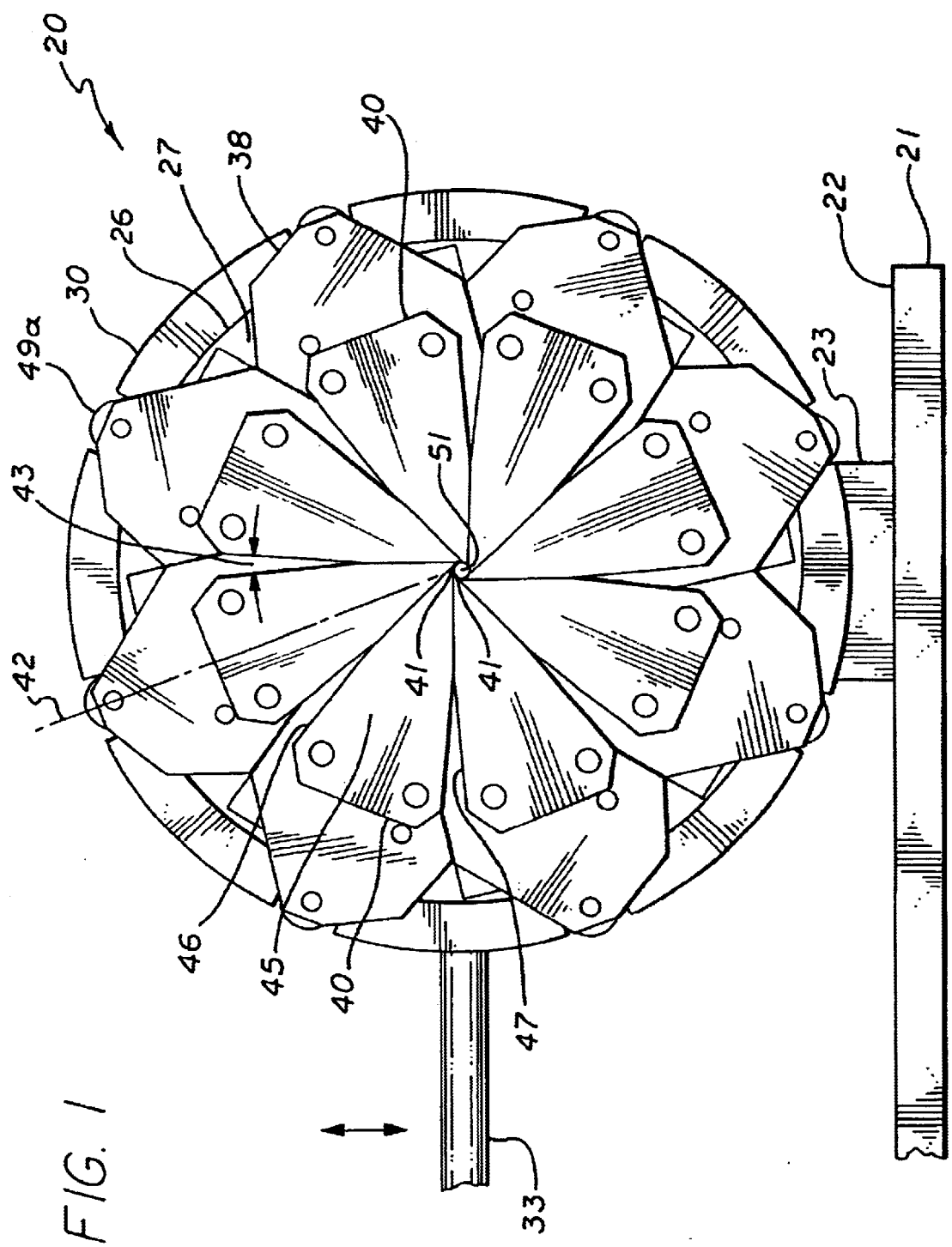
FIG. 1 depicts a front elevational view of the stent crimping assembly.
Figure 2:
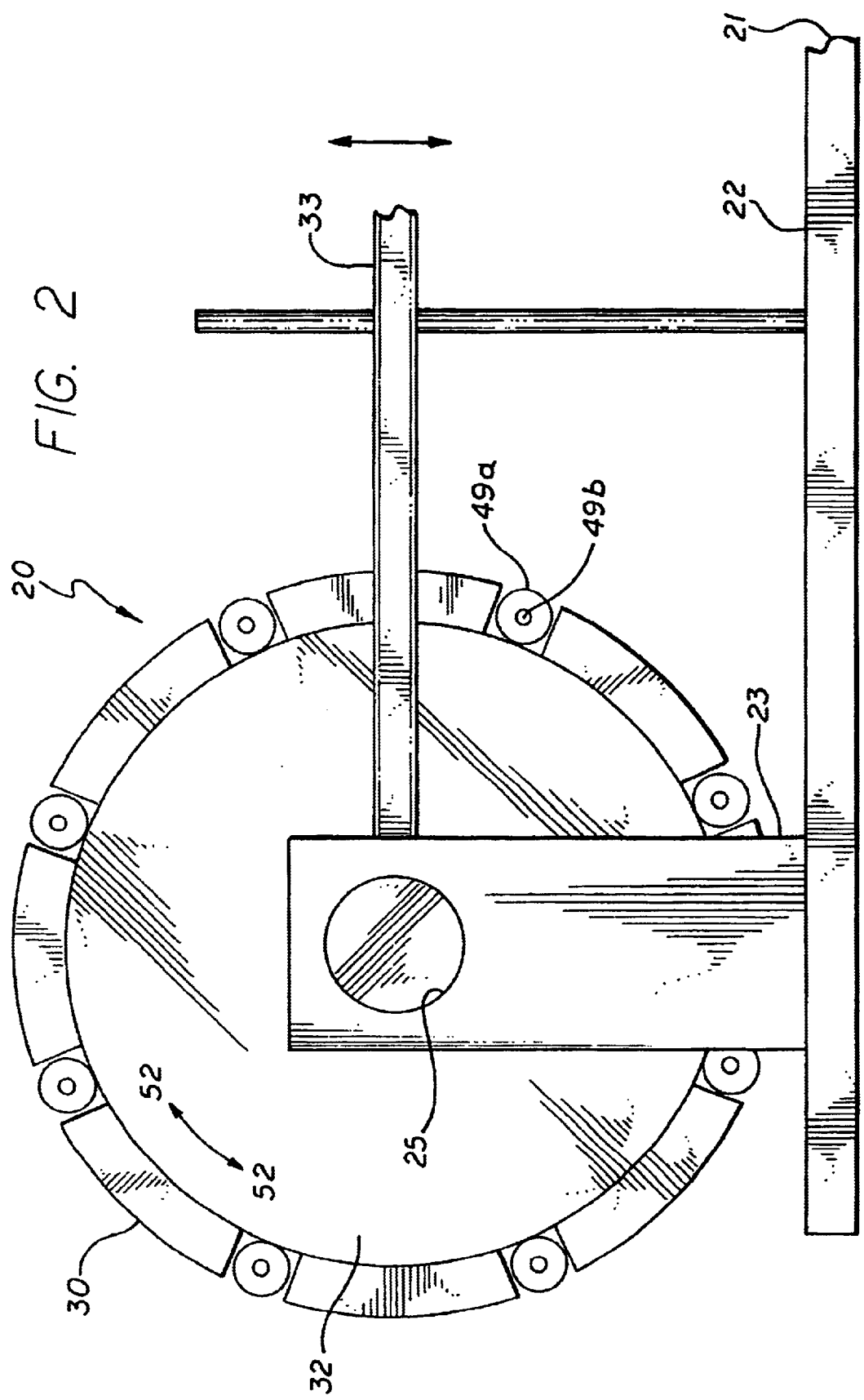
FIG. 2 depicts a rear elevational view of the stent crimping assembly.
Figure 3:
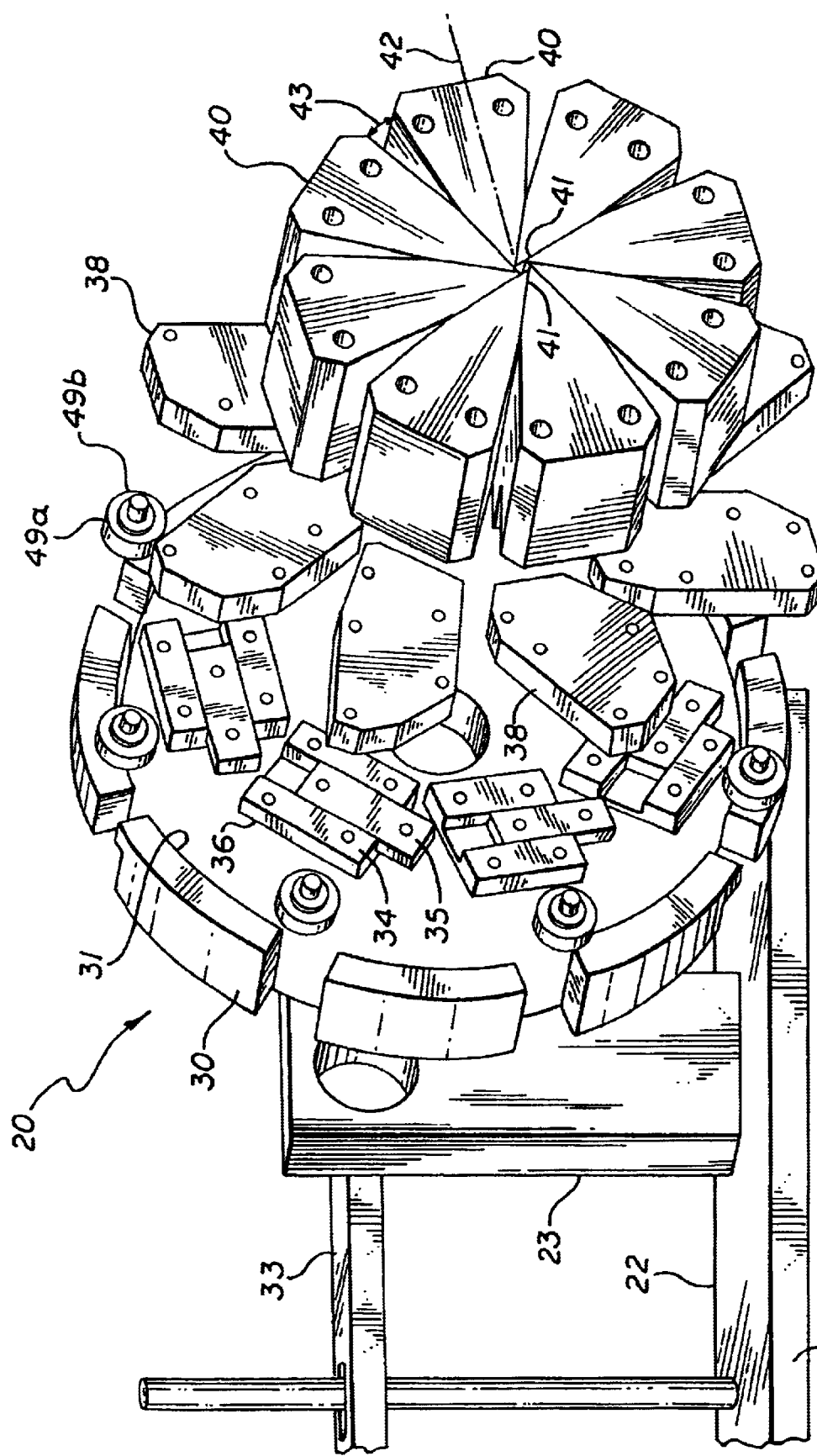
FIG. 3 depicts an exploded perspective view of the stent crimping assembly.

The present invention stent crimping assembly provides for a reliable and uniform crimp of any stent onto a catheter. The stent crimping assembly is capable of crimping almost any size stent, or length of stent, onto the distal portion of a catheter, including stents for coronary arteries and peripheral arteries. The terms crimping and compressing as used herein are meant to be interchangeable and mean that the diameter of the stent is reduced to some degree. Typically, balloon-expandable stents are known by persons having ordinary skill in the art to be "crimped" onto the balloon portion of a catheter while self-expanding stents are compressed onto a mandrel or sheath and then inserted into a catheter. Also, references to "stent crimping assembly" as used herein is not meant to be limiting since the assembly can be used as a measuring device to accurately measure the radial strength of a stent. Thus, for ease of reference, the device has been referred to throughout as a stent crimping assembly, but it also is used to measure the radial strength of a stent. Further, while reference is made herein to crimping or compressing "stents," the invention can be used with any intraluminal device to reduce the diameter or measure radial strength. Thus, the invention is particularly useful with stents, grafts, tubular prostheses, embolic devices, embolic filters, and embolic retrieval devices.

The present invention also can be used to compress a self-expanding stent onto a mandrel or a sheath and then insert the compressed stent into a catheter for subsequent use to repair a vessel. The present invention also can be used to measure the radial force of an expanded or unexpanded stent.

In keeping with the invention as shown in FIGS. 1–4, the stent crimping assembly 20 is composed of a base 21 on which platform 22 is attached. A vertical support column 23 is attached to and extends upwardly from the base. A pair of shafts that are coaxial to each are attached to the support column and extend at a 90° angle from the support column. A rotating shaft 24 is provided for rotational movement and a stationary shaft 25 is coaxial with and extends within the rotating shaft. A first disk 26 is supported by the stationary shaft. In one embodiment, it is preferred that the first disk 26 have no rotational movement and accordingly, is referred to as a stationary disk. The stationary disk 26 has a front face 28 and a rear face 29 as can be seen in the drawings. A second disk 30, referred to herein as a drive disk, is approximately the same diameter as the stationary disk and is mounted on the rotating shaft so that it is adjacent to the stationary disk. The drive disk has a front face and a rear face and is positioned in relation to the stationary disk so that the front face of the drive disk is adjacent to and in relatively close proximity to the rear face 29 of the stationary disk. Rotational movement is imparted to the drive disk by rotating the rotating shaft 24 by any of a number of means.

As illustrated in FIGS. 1–4, a lever 33 is attached to the rotating shaft so that as the lever is moved in a vertical position, the shaft is rotated in either a clockwise or counterclockwise direction. Rotating the shaft in turn rotates the drive disk 30 a corresponding number of degrees. It is contemplated that other means are available to impart rotational movement to the rotating shaft, and in turn the drive disk. For example, an electric motor (not shown) can be attached to the rotational shaft to impart rotational movement. Likewise, either hydraulic or pneumatic means may be employed to impart rotational movement to the rotating shaft. Importantly, the amount of rotation to the shaft, and hence rotation of the drive disk, must be controllable in both the clockwise and counterclockwise direction, as will be more fully described herein. References to a "disk" herein are not meant to be limiting and, although the disclosed disks are circular, they can be other shapes without departing from the invention (e.g., square, oval, rectangular). If the drive disk is not circular, however, then the roller bearing should be carried in an arcuate slot (see FIG. 11).

In further keeping with the invention, the linear slider 34 is attached to the face 28 of the stationary disk. The linear slider has a base 35 which is positioned in a carriage 36 so that the base slides within the carriage. The carriage is attached to the stationary disk typically by attachment screws. As will be described more fully herein, it is the purpose of the linear slider to convert the rotational movement of the drive disk to linear movement of the wedges.

Figure 4:
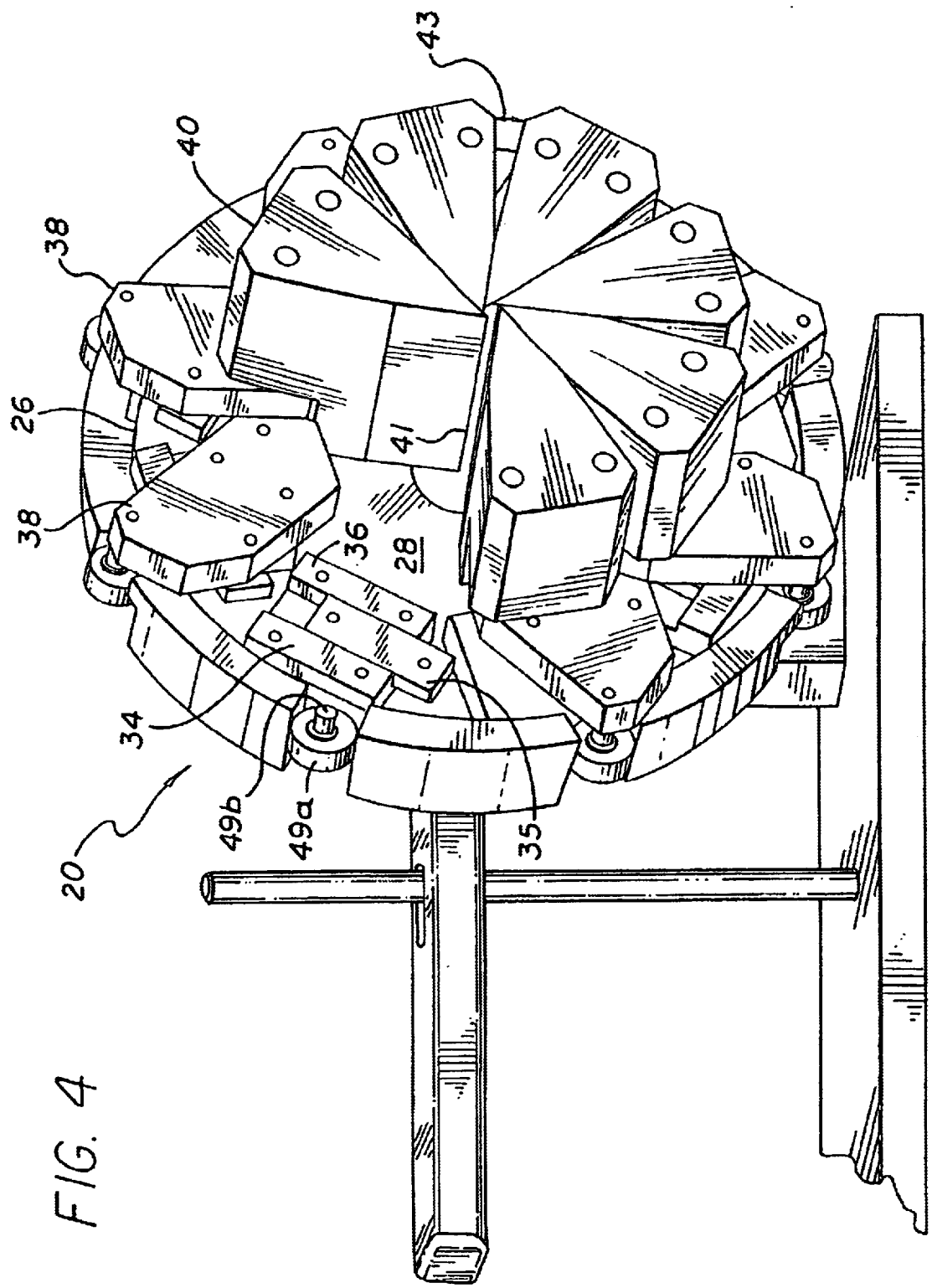
FIG. 4 depicts a partially exploded elevational view of the stent crimping assembly.

As shown in FIG. 4, a bracket 38 is attached to the linear slider, and more appropriately to the base 35 of the linear slider. The bracket can have essentially any configuration and is intended to be carried linearly by the linear sliding movement of the base 35.

In order to impart a crimping or compressing force on a stent, moving elements are provided. The moving elements are referred to herein as wedges, which in one embodiment have a generally triangular shape. In other embodiments, the moving elements or wedges may have other shapes, such as a knife blade as shown and described later. One side of the moving element includes a section that comes into contact with a stent and crimps it onto a catheter. This section of the moving element or wedge is substantially linear and is referred to as the stent- or device-contacting section, region or portion.

As shown in FIGS. 1–5, and in particular FIGS. 5a–5e, a plurality of moving elements 40 or wedges are attached to the bracket so that wedges will have the same linear movement as does the bracket, which is attached to the linear slider. Each of the wedges has two sides 46 and 47 which meet to define a tip 41. Those portions of each side that are immediately adjacent the tip 41 i.e., exterior edges 46a and 47a, define a tip region angle θ. The wedge has a top 45 and a bottom 44 so that the wedge bottom attaches to the bracket 38 by any convenient means, including attachment screws, adhesives, and the like. Bracket 38 can have any shape, and in fact is unnecessary. The bracket is provided as a spacer between the wedges 40 and the linear slider. The wedges in fact could be formed such that the wedge bottom 44 is in the form of the bracket so that the wedges and the brackets are all one piece.

Figure 5D:
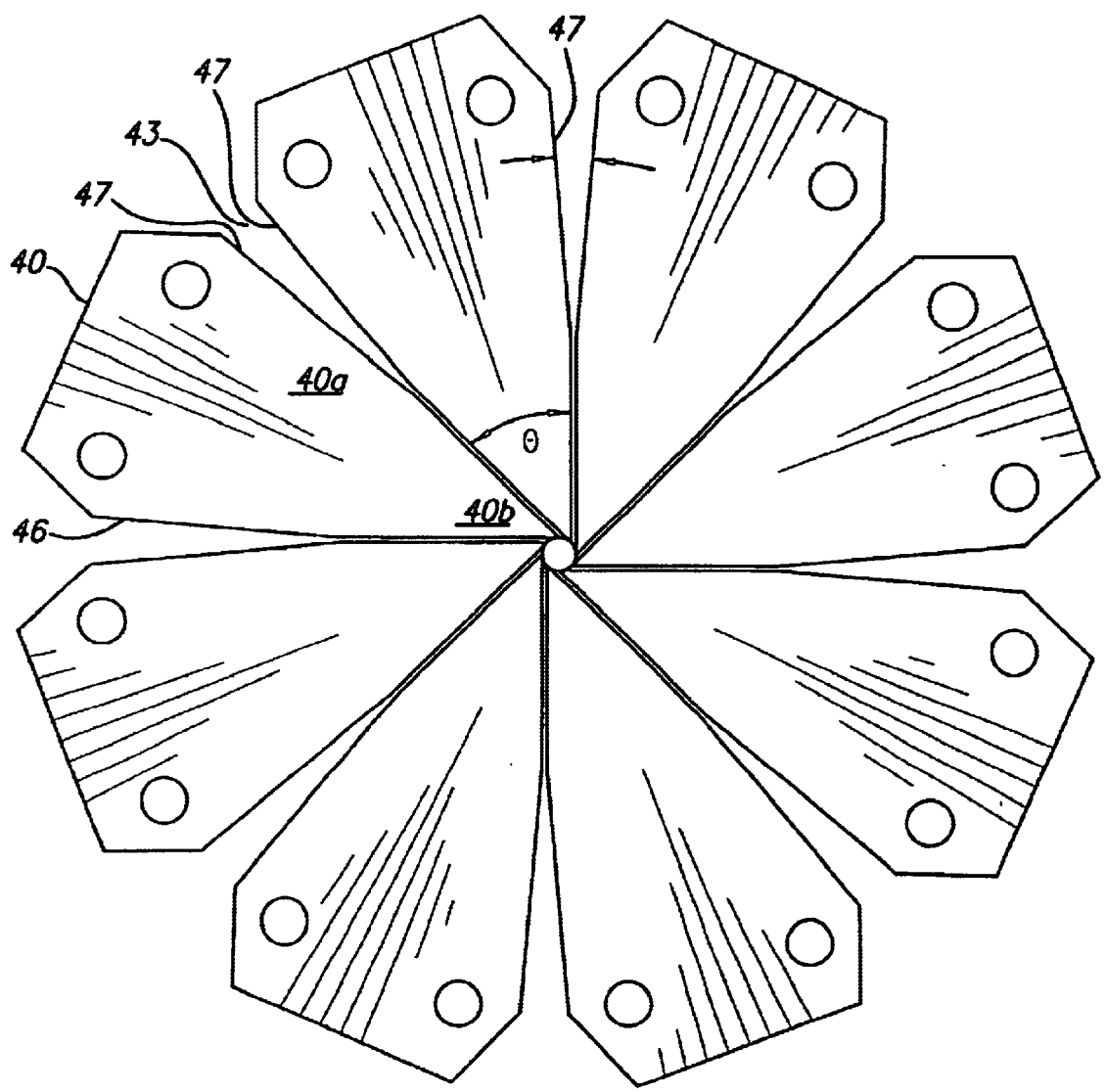
FIG. 5d depicts a front view of the moving elements of FIG. 4 wherein the space between adjacent elements is shown.
Figure 6:
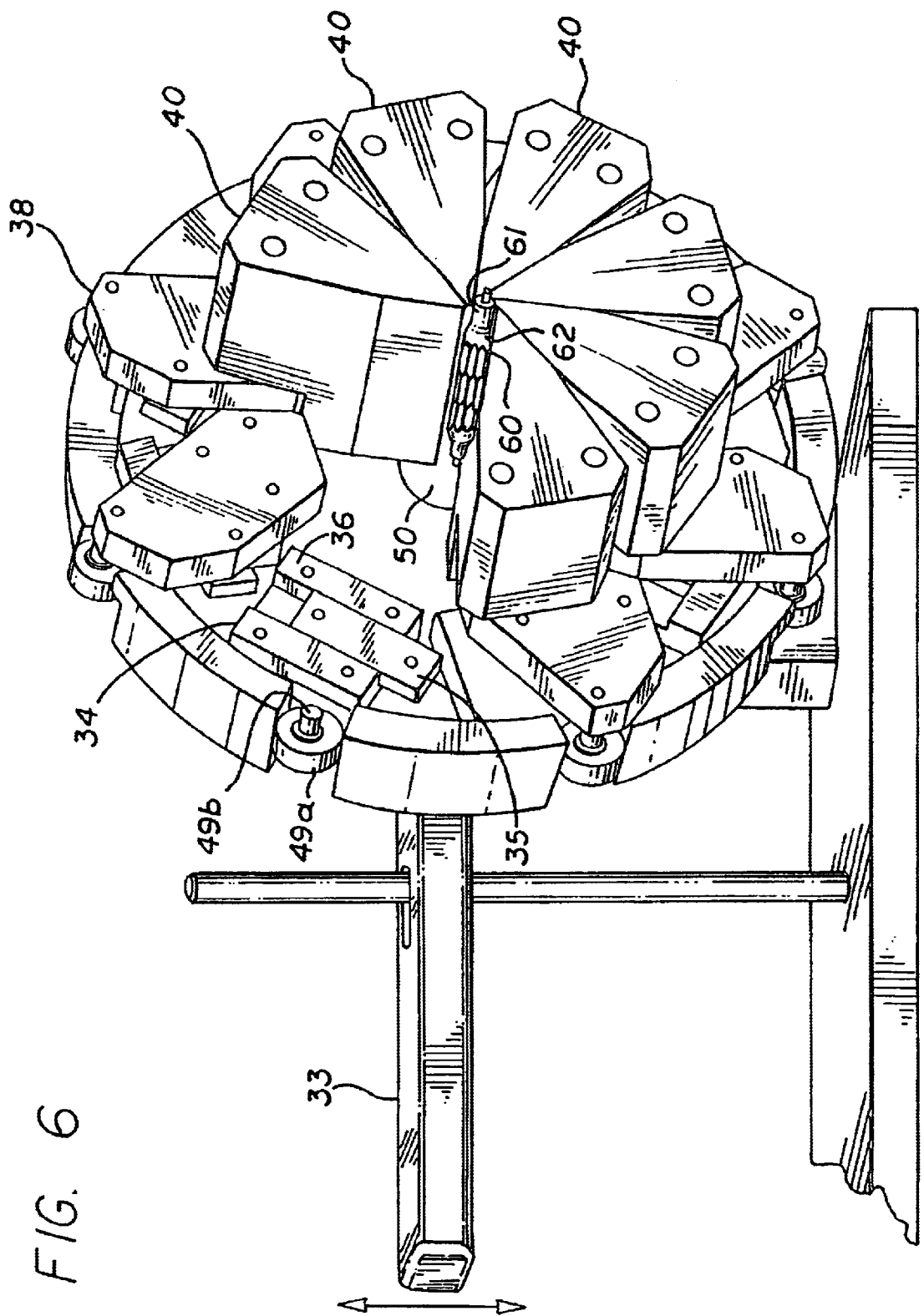
FIG. 6 depicts a perspective view of the stent crimping assembly with a stent premounted on a catheter positioned in the opening of the assembly.
Figure 6A:
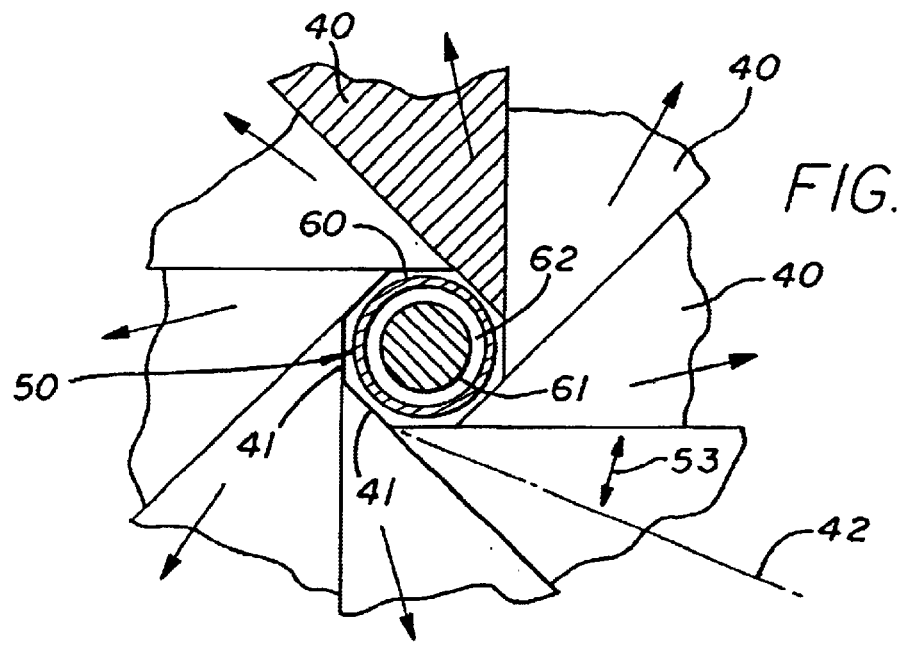
Figure 7A:
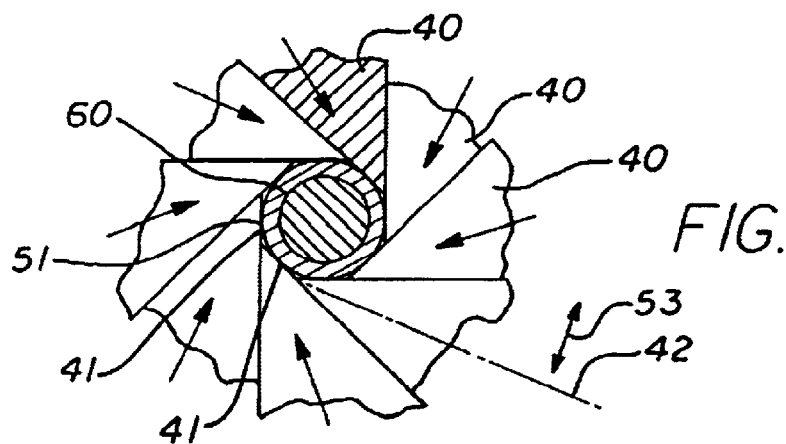
FIG. 7 depicts the stent crimping assembly of FIG. 6 where the moving elements have been linearly moved toward the closed position.
Figure 8A:
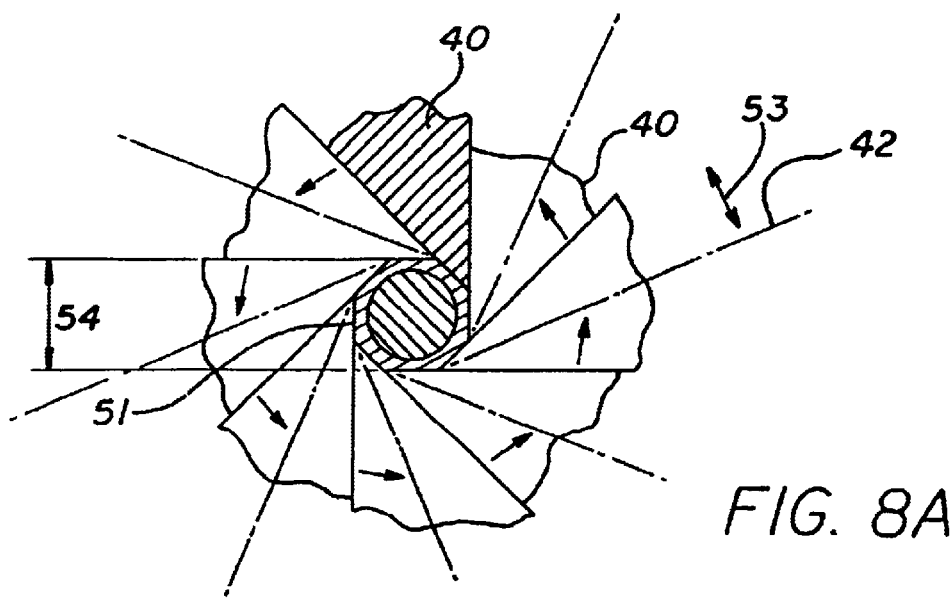
FIG. 8 depicts the stent crimping assembly of FIG. 6 where the moving elements have been moved linearly toward the closed position and into crimping engagement with the stent.
Figure 7:
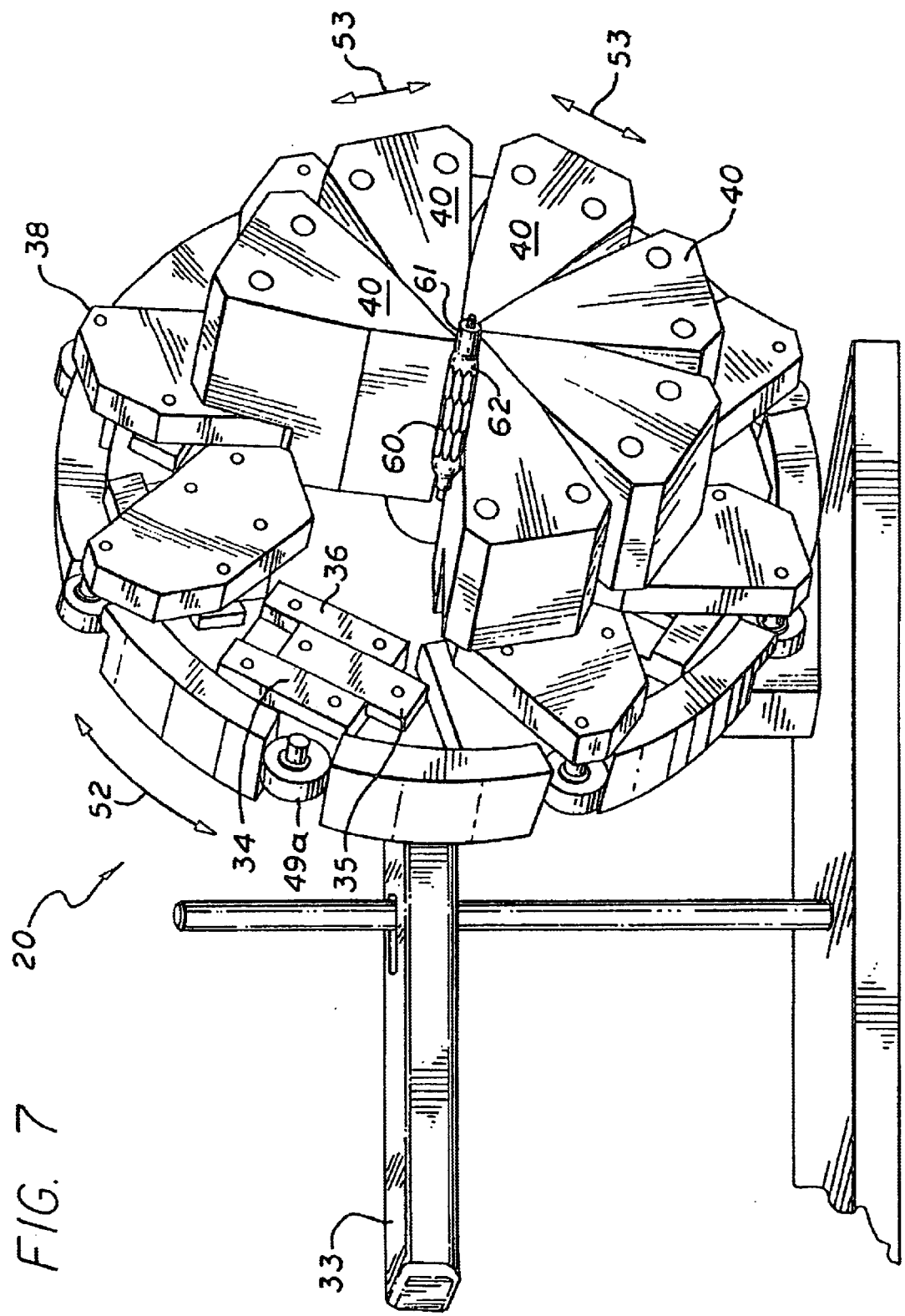
Figure 9:
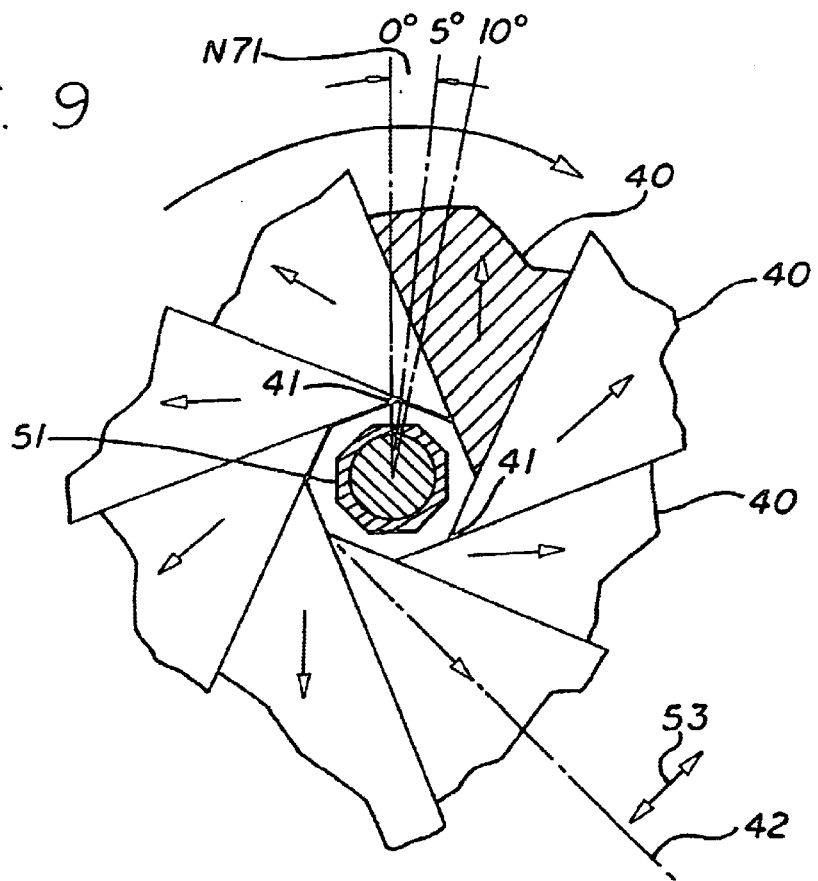
FIG. 9 depicts the stent crimping assembly of FIG. 6 where the moving elements have moved linearly toward the open position and the stent, now mounted on the catheter, is withdrawn from the assembly.
Figure 10:
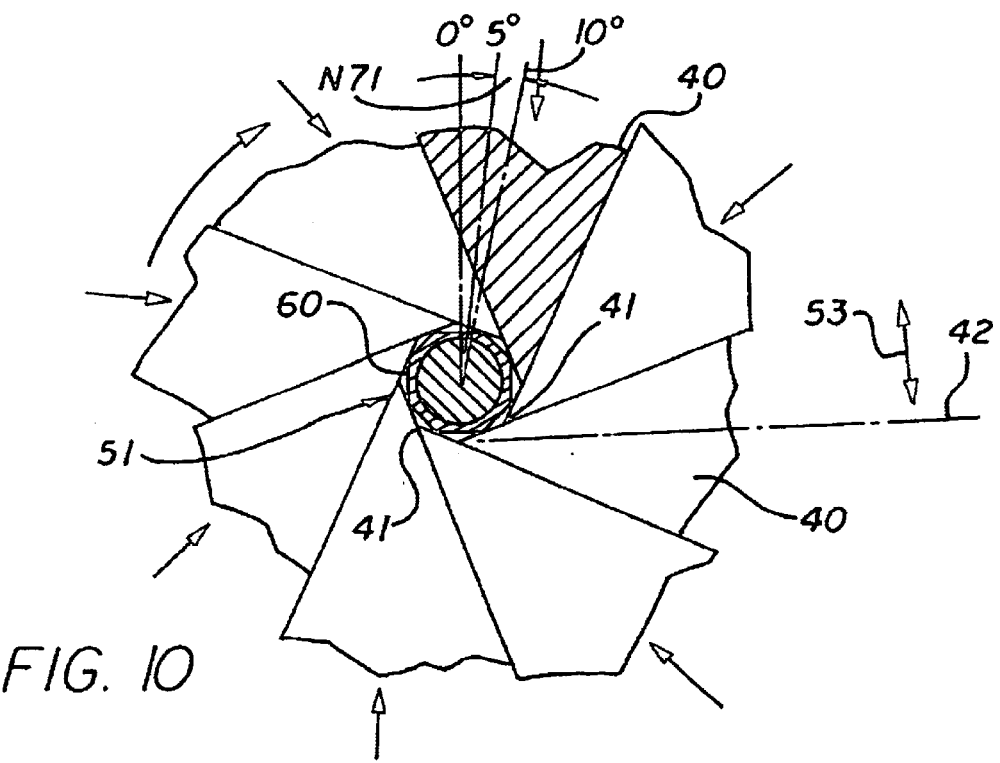
FIG. 10 depicts the stent crimping assembly of FIG. 6 being indexed N degrees for subsequent crimping procedures.

As shown in the drawings, particularly FIG. 5d, it is important that there is a spacing 43 between the wedges 40 so that they can move relative to one another in a substantially friction-free manner. The amount of spacing between the wedges is dependent upon several factors, including the number of wedges used in the assembly. Accordingly, the spacing is dependent upon the specific application, keeping in mind that it is important to reduce the amount of friction in the assembly during the crimping operation. As shown more clearly in FIG. 5c, wedge angle α 48 is defined by the difference between the taper of edges 46a, 47a immediately adjacent the tip 41 and the balance of each side 46, 47 of the wedge. The angle α can vary as desired and typically will be greater or lesser depending upon the number of wedges used in the stent crimping assembly. Preferably, the stent crimping assembly will have between three and eight wedges, and more preferably eight wedges are desirable to provide a uniformly crimped stent. The number of wedges used can be increased or decreased depending on the particular application.

With reference to FIG. 5d, in order to provide substantially friction-free movement among the wedges, the spacing 43 between adjacent wedges 40 extends along the entire length of the sides 46, 47 of the wedges. As previously described, the spacing 43 between adjacent upper regions 40a of the wedges is defined by the angle α 48. The spacing 43 between adjacent tip regions 40b of the wedges is defined by the tip-region angle θ which is the angle formed between the taper edges 46a, 47a of each wedge. In order to maintain spacing between adjacent wedges in the tip region, the summation of the θ angles for all wedges is less than 360° In one configuration of the stent crimper, eight wedges, each having an angle θ of just less than 45°, e.g. 44.3°±0.3°, form an octagon opening 70 (FIG. 5e) having a center 72. The gap between adjacent tip regions 40b is substantially uniform along the length of the tip regions.

"With reference to FIGS. 5c, 5d and 5e, each element 40 has a first side 46 and a second side 47 joining at a tip 41. The first side 46 includes a substantially linear region 46a, a portion of which contacts the stent during the crimping process. The moving elements 40 are arranged such that the tip 41 of each element is spaced (as shown in FIG. 5d) from the first side 46 of an adjacent moving element and is located more adjacent to the first side 46 of the adjacent element than the second side 47 of the adjacent element. Thus, for example, while element B of FIG. 5e has two adjacent elements, element A and element C, only one of them (element C) is positioned relative to element B such that the tip 41 of element B is located more adjacent to the first side 46 of the element than the second side 47 of the element."

In order to impart linear motion to the wedges, a roller 49a and roller arm 49b are attached to the assembly. Specifically, roller arm 49b is attached to the brackets 38 and the roller 49a is in contact with drive disk 30. As rotational movement is imparted to the drive disk, it is also imparted to the roller and the roller arm, which in turn imparts movement to the brackets. Since the brackets are attached to the linear slider 34, the brackets, and hence the wedges, can only move in a linear direction. The roller minimizes any friction between the rotational movement of the drive disk and the linear movement imparted to the brackets and the wedges. Other means are available to connect the brackets to the drive disk including a member without a roller, however, it is important to reduce the friction so that the assembly operates smoothly.

With reference to FIG. 5e, the side 46a of each wedge tip region 40b facing the opening 70 forms an exterior angle with the same side 46a of an adjacent wedge tip region 40b. The exterior angle is that angle formed between the adjacent sides 46a on the outside of the opening 70 and has a bisect 42. Due to the number of wedges in this configuration, the exterior angle is acute. As the brackets move in a linear fashion, the linear movement imparted to the wedges 40 thereby is perpendicular to the bisect 42 associated with the wedge. Accordingly, the tip 41 of each wedge 40 moves linearly in a direction that also is perpendicular to the bisect 42. The linear path 74 of movement followed by the tip 41 terminates at or near the center 72 of the opening 70 formed by the wedges 40.

The stent crimping assembly has an open position 50 and a closed position 51 as shown in FIGS. 6–10. As rotational movement 52 is imparted to the drive disk, the tips 41 of the wedges 40 move linearly away from the center of the opening formed by the wedges and toward the open position. When the drive disk is rotated in the opposite direction, the tips of the wedges move toward the center of the opening toward the closed position. The linear movement 53 of the wedges creates a parallel gap 54 with respect to wedges that are 180° opposite to each other on the stationary disk. In other words, the sides of the wedges that are 180° opposite of each other move in a linear fashion and define the parallel gap.

One method for crimping the stent onto a catheter includes multiple applications of crimping force by the moving wedges onto the stent. A stent 60 is first premounted onto a catheter 61, preferably near the distal end thereof. Preferably, the catheter will have an inflatable expandable member 62, generally an inflatable balloon, upon which the stent is first premounted. The stent and the balloon portion of the catheter are positioned within the stent crimping assembly 20 when the wedges are in the open position 50. The drive disk is rotated as previously described to impart rotational movement which is transmitted to the roller 49*a*. The rotational movement is imparted to the brackets and wedges, which is converted to linear movement by the linear slider 34. As the wedges move linearly toward the closed position 51, a portion of the device-contacting region of the first side of each wedge comes into contact with the stent. As further rotational movement is imparted, the wedges continue to move in a linear direction and continue to move toward the closed position thereby imparting crimping force on the stent. Preferably, eight moving wedges are used to impart crimping force on the stent so that when initially crimped the stent will have the appearance of an octagon when viewed under magnification. In order to form a more perfect cylinder on the stent, it may be desirable to repeatedly crimp the stent by slightly rotating the stent and catheter a few degrees and then applying further crimping force. The opening and closing of the moving wedges in this manner will provide a stent that is tightly crimped onto the catheter and will have the appearance of a substantially perfect cylinder when viewed under magnification.

It may be desirable to measure or limit the amount of force imparted by the wedges onto the stent, and this can be accomplished by any number of means including providing mechanical or electrical stopping switches which limit the closing position of the wedges. By limiting how far the wedges can close, the amount of force also will be limited. The geometric position of the wedges also can indicate how much force is being applied to the stent. Strain gauges also can be attached to the wedges to measure the amount of force being applied to the stent and catheter and can be controlled and monitored to limit the amount of crimping force applied to the stent.

In an alternative embodiment, the drive disk 30 and the stationary disk 26 can be indexed a preselected number of degrees N 71. In this embodiment, the stent and catheter are held stationary within the opening of the stent crimping assembly. The stent is crimped in the manner described, and then the stationary disk and the drive disk are rotated N number of degrees form a 0° position and crimping force is again applied. This procedure is repeated each time the stationary disk and the drive disk are indexed N number of degrees. As an example, the stationary disk and drive disk can be indexed starting from a 0° position every 5° up to 45°, and at every 5° position, the stent is crimped. The stationary disk and drive disk are then moved back to the 0° position and rotated in the opposite direction in 5° increments for 45°, and the stent is crimped at each 5° increment. By crimping the stent multiple times at various degrees along the cylinder, the stent is more uniformly and tightly crimped onto the balloon portion of the catheter so that under magnification it will appear as a substantially perfect cylinder.

Figure 11:
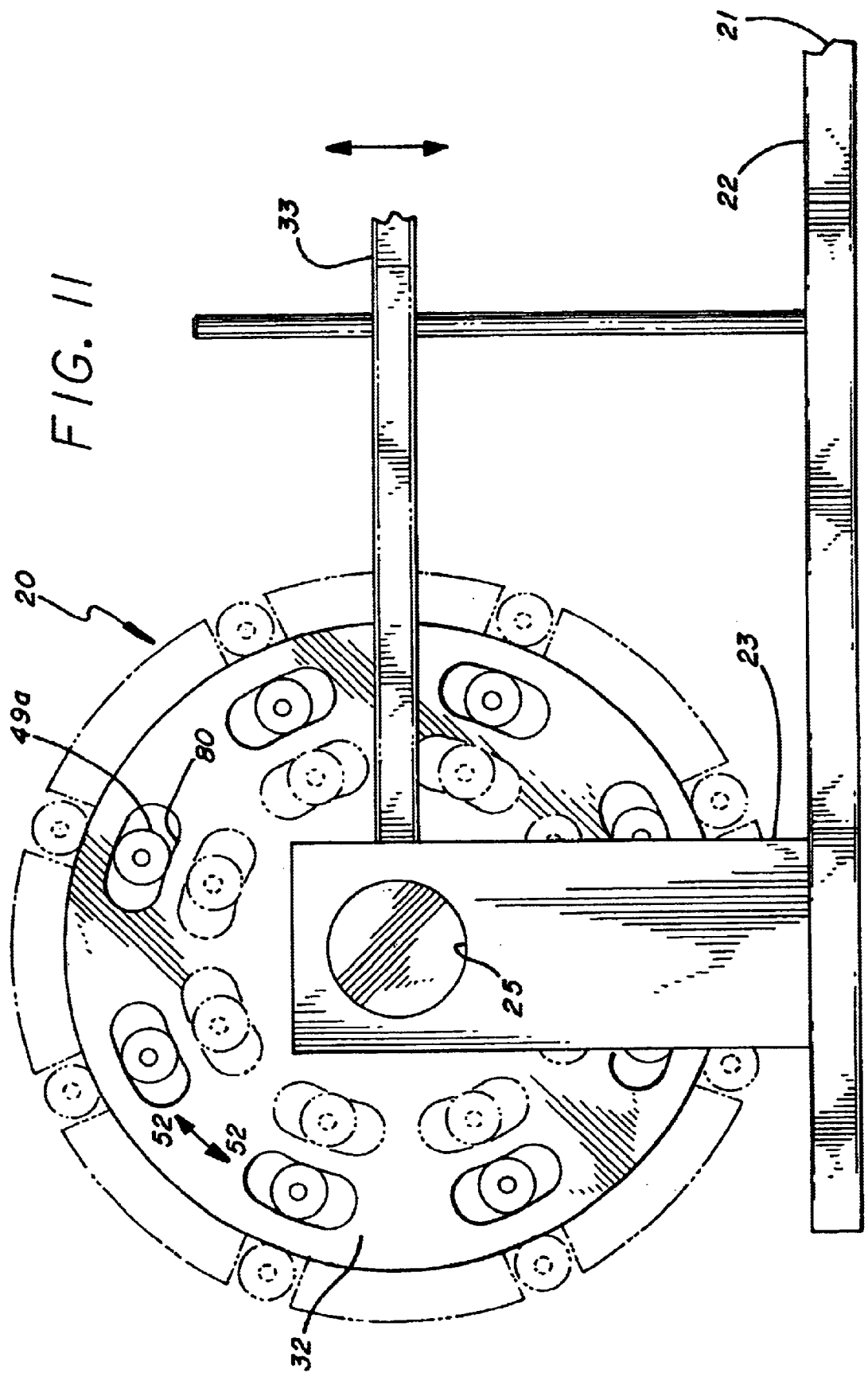
FIG. 11 depicts a rear elevational view of the stent crimping assembly showing different locations for the roller bearing.

In an alternative embodiment of the invention, the stent assembly can be used to measure the radial force of a balloon-expandable or a self-expanding stent. In this embodiment, the roller-bearing 49*a*, as shown in FIG. 11, would be moved radially outwardly away from the wedges 40. The farther the rolling bearing is from the apex of the wedges, the less force the wedges apply to the stent. Thus, the roller bearing can be positioned so that as the wedges are moved toward the closed position 51 with an unexpanded or expanded stent positioned within the opening formed by the wedges, the radial force of the stent can be measured by the assembly. As the wedges continue to move toward the closed position, they will have a tendency to crush the stent and in so doing the resistance to crushing is measurable, and is determinative of the radial strength of the stent. Different stent patterns will have different radial strengths that can be quantified and measured by the present invention in the manner described. Again, an important feature of being able to measure accurately the radial strength of the stent, the rollers provide a near frictionless movement along with the substantially friction-free movement among the wedges, which all contribute to an accurate measurement of the radial strength of the stent. Likewise, moving the roller bearing 49*a* radially closer to the apex of the wedges, as shown in phantom in FIG. 11, results in a greater force applied to the wedges and hence the stent. An arcuate slot 80 is provided for the roller bearing to travel in.

The stent crimping assembly may be formed of plastic and metal parts, however, either all plastic or all metal, or a combination of both, is desirable. For example, both the stationary disk 26 and drive disk 30 can be formed of a polymer including a hard plastic that is machinable. The wedges 40 and brackets 38 also can be formed of a polymer that is machinable so that precise tolerances can be machined into the wedge angle $\alpha$ 48 and the tip region angle $\theta$ to insure that the wedges move relative to one another without substantial friction. The rotating and stationary shaft can be formed of a conventional shaft material and all attachments can be in the form of metal screws, adhesives or any other conventional attachment means.

In a preferred embodiment, most of the parts of the stent crimping assembly are made from machined polymers, however, the present invention is also well suited to be made from surgical steel, aluminum, or other metals so that it can be used multiple times.

Figure 12:
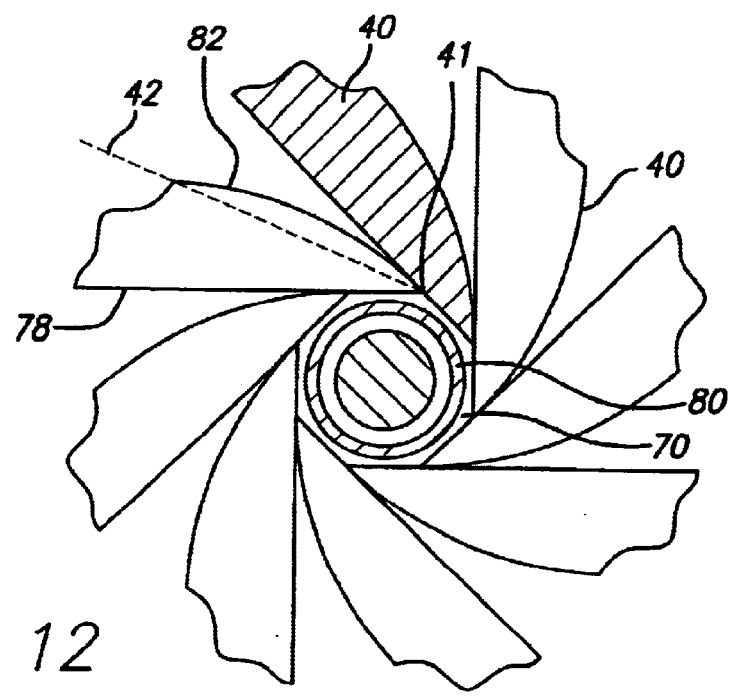
FIG. 12 depicts an alternate configuration of the moving elements.

With reference to FIG. 12, as previously mention, the moving elements 40 or wedges may have anyone of a variety of shapes, as long as one side of the element includes a substantially straight region for contacting the stent, i.e., the stent-contacting region. To this end, in an exemplary alternate configuration, the siding elements 40 are shaped like knife blades, with a straight side 78 facing the opening 70 where a stent 80 may be placed to thereby provide the stent-contacting region and an arcuate side 82 facing away from the opening. The straight sides 78 of adjacent moving elements 40 from an exterior angle having a bisect 42. As with the previously described wedge configuration, linear movement of the brackets to which the moving elements 40 are attached translates to linear movement of the elements in a direction perpendicular to the bisect 42. Though not evident from FIG. 12, in a preferred embodiment of this configuration, there is a space between the arcuate side 82 of each blade and the linear side 78 of its immediate adjacent blade.

Figure 13:
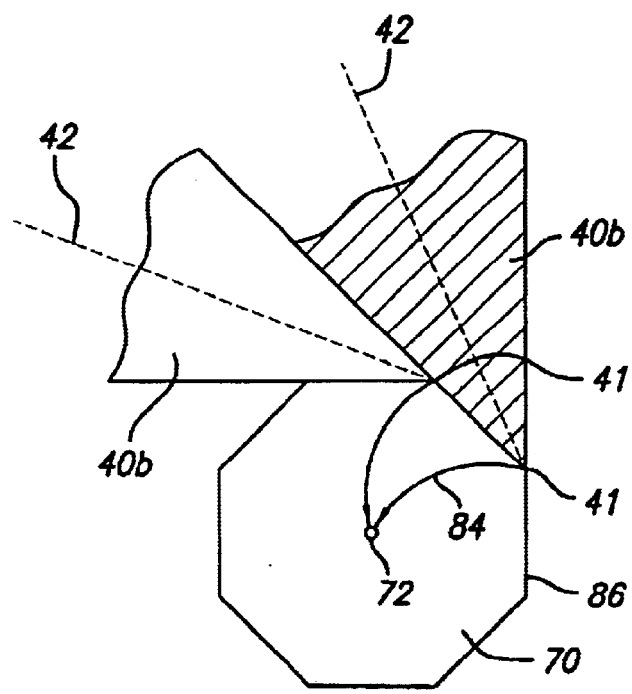
FIG. 13 depicts the paths traveled by the moving elements in another configuration of the assembly.

In another embodiment of the stent crimper, the first disk 26 is configured for rotation relative to the second disk 30, which is fixed in place. All other assembly elements, e.g., linear sliders, brackets, rollers, etc., remain as previously described with respect to the other embodiment. With reference to FIGS. 4 and 13, in this embodiment, rotation of the first disk 26 relative to the second disk 30 causes the moving element 40 to experience both linear and rotational movement. Accordingly, the tip region 40b and the tip 41 of each moving element travels along an arcuate path 84 between the perimeter 86 of the opening 70 defined by the elements and the center 72 of the opening.

Other modifications can be made to the present invention without departing from the scope thereof. The specific dimensions, procedural steps, and materials of construction are provided as examples, and substitutes are readily contemplated which do not depart from the invention.

What is claimed:

1. A crimping assembly comprising:
    a plurality of spaced apart moving elements, each element having a first side and a second side joining at a tip, wherein the space between adjacent elements extends along the length of the first and second sides and the first side includes a substantially linear region, wherein the substantially linear region forms a crimping surface throughout a crimping process, the tip being spaced from the first side of an adjacent moving element and more adjacent to the first side of the adjacent element than the second side of the adjacent element, the first side of the moving element forming an acute angle with the first side of the adjacent moving element, the moving elements arranged relative to each other such that the substantially linear regions of the first sides form an opening having a center and a polygonal shape; and
    each moving element being configured for non-radial movement relative to the center of the opening, wherein the moving elements are associated with a first disk and a second disk, the disks configured for rotational movement relative to each other, whereby, as one of the first and second disks rotates, the tip of each moving element moves toward the center of the opening.

2. The assembly of claim 1 configured such that:
    the second disk is fixed in position;
    the first disk rotates relative to the second disk; and
    the tip of each moving element moves along an arcuate path from a point on the perimeter of the opening toward the center of the opening when the first disk is rotated in a first direction.

3. The assembly of claim 2 wherein the tip of each moving element moves along an arcuate path away from the center of the opening when the first disk is rotated in a second direction opposite the first direction.

4. The assembly of claim 1 wherein the first side of the moving element includes a substantially linear device-contacting region and the second side of the moving element includes a substantially linear region.

5. The assembly of claim 4 wherein the substantially linear regions of the first and second sides of each moving element define a tip-region angle and the sum of the tip-region angles for all moving elements is less than 360°.

6. The assembly of claims 5 comprising eight moving elements, each with a tip-region angle of less than 45°.

7. The assembly of claim 6 wherein the tip-region angle is 44.3°±3°.

8. The assembly of claim 1 wherein the first side of the moving element includes a substantially linear device-contacting region and the second side of the moving element is nonlinear.

9. The assembly of claim 8 wherein the second side is curved.

10. An assembly for crimping an intraluminal device onto a catheter, comprising:
    first and second disks configured for rotational movement relative to each other, each disk having a front face and a rear face;
    a plurality of linear sliders attached to the front face of the first disk; and
    a plurality of spaced apart moving elements, each element having a first side and a second side joining at a tip, wherein the space between adjacent elements extends along the length of the first and second sides and the first side includes a substantially linear region, wherein the substantially linear region forms a crimping surface throughout a crimping process, the tip being spaced from the first side of an adjacent moving element and more adjacent to the first side of the adjacent element than the second side of the adjacent element, the first side of the moving element forming an acute angle with the first side of the adjacent moving element, the moving elements arranged relative to each other such that the substantially linear regions of the first sides form an opening having a center and a polygonal shape, each moving element attached to a linear slider and to the second disk;
    whereby each of the moving elements is configured for non-radial movement relative to the center of the opening and as one of the first and second disks is rotated, the tip of each moving element moves toward the center of the opening.

11. The assembly of claim 10 configured such that:
    the second disk is fixed in position;
    the first disk rotates relative to the second disk; and
    the tip of each moving element moves along an arcuate path from a point on the perimeter of the opening toward the center of the opening when the first disk is rotated in a first direction.

12. The assembly of claim 10 wherein the tip of each moving element moves along an arcuate path away from the center of the opening when the first disk is rotated in a second direction opposite the first direction.

13. The assembly of claim 12 wherein rotation of the first disk is limited.

14. The assembly of claim 10 wherein a plurality of brackets are positioned between the plurality of moving elements and the plurality of linear sliders, the brackets being attached to the moving elements and to the linear sliders.

15. The assembly of claim 10 wherein the assembly is configured such that the first disk and the second disk may be collectively rotated relative to the intraluminal device a preselected number of degrees N.

16. The assembly of claim 15 wherein the assembly is configured such that the first and second disks may be repeatedly rotated N degrees around the intraluminal device.

17. The assembly of claim 16 wherein the number of degrees of rotation N is variable from about 1° to about 20°.

18. The assembly of claim 15 wherein the number of degrees of rotation N is 5°.

19. The assembly of claim 15 wherein the first disk and the second disk rotate in one direction only.

20. The assembly of claim 15 wherein the first disk and the second disk rotate in either direction.

21. A method for compressing an intraluminal device onto a catheter, a mandrel or a sheath, comprising:

providing a compressing assembly having first and second disks mounted on a base, a plurality of spaced apart moving elements attached to a corresponding plurality of linear sliders on the first disk and to the second disk, each element having a first side and a second side joining at a tip, wherein the space between adjacent elements extends along the length of the first and second sides and the first side includes a substantially linear region, wherein the substantially linear region forms a compressing surface throughout a compressing process, the tip being spaced from the first side of an adjacent moving element and more adjacent to the first side of the adjacent element than the second side of the adjacent element, the first side of the moving element forming an acute angle with the first side of the adjacent moving element, the elements arranged such that the substantially linear regions of the first sides form an opening having a center and a polygonal shape, the elements configured for movement relative to each other such that the spacing between the elements provides substantially frictionless movement among the elements;

imparting a first rotational movement to one of the first and second disks which translates movement to the moving elements so that the tips of the moving elements move along a path away from the center of the opening, wherein the movement of the moving elements is non-radial relative to the center of the opening;

providing an intraluminal device pre-mounted on a catheter and positioning the intraluminal device within the opening;

imparting a second rotational movement to the previously rotated disk which translates movement to the moving elements so that the tips of the moving elements move along a path toward the center of the opening and a portion of the first sides of the moving elements move into contact with the intraluminal device, wherein the movement of the moving elements is non-radial relative to the center of the opening;

compressing the intraluminal device onto the catheter, mandrel or sheath by continuing to move the tips of the moving elements along a path toward the center of the opening;

imparting a third rotational movement to the previously rotated disk which translates movement to the tips of the moving elements along a path away from the center of the opening, wherein the movement of the moving elements is non-radial relative to the center of the opening; and removing the intraluminal device and catheter or mandrel or sheath from the compressing assembly.

22. The method of claim 21 wherein:

the second disk is fixed in position;

the first, second and third rotational movements are applied to the first disk; and the path of each tip is along an arcuate path from a point on the perimeter of the opening toward the center of the opening.

23. The method of claim 21 wherein the first and third rotational movements are in a direction opposite the second rotational movement.

24. A crimping assembly comprising:

a plurality of spaced apart moving elements, each element having a first side and a second side joining at a tip, wherein the space between adjacent elements extends along the length of the first and second sides and the first side includes a substantially linear region, wherein the substantially linear region forms a crimping surface throughout a crimping process, the tip being spaced from the first side of an adjacent moving element and more adjacent to the first side of the adjacent element than the second side of the adjacent element, the first side of the moving element forming an exterior angle with the first side of the adjacent moving element, the moving elements arranged relative to each other such that the substantially linear regions of the first sides form an opening having a center and a polygonal shape; and each moving element being configured for non-radial movement relative to the center of the opening, wherein the moving elements are associated with a first disk and a second disk, the disks configured for rotational movement relative to each other, whereby, as one of the first and second disks rotates, the tip of each moving element moves toward the center of the opening.

25. The assembly of claim 24 configured such that:

the second disk is fixed in position;

the first disk rotates relative to the second disk; and the tip of each moving element moves along an arcuate path from a point on the perimeter of the opening toward the center of the opening when the first disk is rotated in a first direction.

* * * * *

UNITED STATES PATENT AND TRADEMARK OFFICE
CERTIFICATE OF CORRECTION

| | | |
|---|---|---|
| PATENT NO. | : 6,840,081 B2 | Page 1 of 1 |
| APPLICATION NO. | : 10/298424 | |
| DATED | : January 11, 2005 | |
| INVENTOR(S) | : Arkady Kokish | |

It is certified that error appears in the above-identified patent and that said Letters Patent is hereby corrected as shown below:

<u>Title Page,</u>
Item 56, U.S. Patent Documents, insert --4,081,092    Cho et al.    7/1978--.
Item 57, Abstract, line 8, delete "move is a" and insert --move in a--.

<u>Column 5,</u>
Line 11-12, delete second occurrence of "where it is tightly crimped onto the mandrel".

<u>Column 8,</u>
Line 31, delete " " " (quotation mark).
Line 44, delete " " " (quotation mark).

<u>Column 10,</u>
Line 59, delete "mention" and insert --mentioned--.
Line 60, delete "anyone" and insert --any one--.

Signed and Sealed this

Fifth Day of December, 2006

JON W. DUDAS
*Director of the United States Patent and Trademark Office*